United States Patent [19]
Yoshii et al.

[11] Patent Number: 5,461,474
[45] Date of Patent: Oct. 24, 1995

[54] INSPECTION APPARATUS FOR DETECTING FOREIGN MATTER ON A SURFACE TO BE INSPECTED, AND AN EXPOSURE APPARATUS AND A DEVICE MANUFACTURING METHOD USING THE SAME

[75] Inventors: Minoru Yoshii, Tokyo; Noriyuki Nose, Atsugi; Masayuki Suzuki, Hadano; Kyoichi Miyazaki, Mitaka; Toshihiko Tsuji, Ayase; Seiji Takeuchi, Kawasaki, all of Japan

[73] Assignee: Canon Kabushiki Kaisha, Tokyo, Japan

[21] Appl. No.: 266,512

[22] Filed: Jun. 27, 1994

[30] Foreign Application Priority Data

Jul. 29, 1993 [JP] Japan ..................... 5-207078

[51] Int. Cl.$^6$ ................................. G01N 21/88
[52] U.S. Cl. ................................. 356/237
[58] Field of Search .................. 356/237, 394, 356/398, 431

[56] References Cited

U.S. PATENT DOCUMENTS

| | | | |
|---|---|---|---|
| 4,274,748 | 6/1981 | Burtin et al. ................. | 356/432 |
| 4,492,472 | 1/1985 | Asano et al. ................. | 356/394 |
| 4,791,586 | 12/1988 | Maeda et al. ................. | 356/237 |
| 5,028,797 | 7/1991 | Abe et al. ................... | 250/548 |
| 5,148,037 | 9/1992 | Suda et al. .................. | 250/548 |
| 5,200,800 | 4/1993 | Suda et al. .................. | 356/401 |
| 5,270,794 | 12/1993 | Tsuji et al. ................. | 356/371 |
| 5,291,023 | 3/1994 | Hasegawa et al. ............. | 250/548 |
| 5,313,272 | 5/1994 | Nose et al. .................. | 356/375 |
| 5,329,359 | 7/1994 | Tachikawa .................... | 356/398 |
| 5,333,050 | 7/1994 | Nose et al. .................. | 356/356 |

FOREIGN PATENT DOCUMENTS 1280473 7/1972 United Kingdom ................... 356/395

Primary Examiner—Richard A. Rosenberger
Attorney, Agent, or Firm—Fitzpatrick, Cella, Harper & Scinto

[57] ABSTRACT

When inspecting the presence of foreign matter on a surface to be inspected by scanning the surface with a light beam from a light source utilizing a scanning system, and receiving scattered light from the surface by a detector, a correlation is utilized between a signal representing first scattered light obtained from the detector when the light beam scans a first line on the surface, and a signal representing second scattered light obtained from the detector when the light beam scans a second line displaced from the first line by a predetermined amount in a direction orthogonal to the direction of the first line.

26 Claims, 17 Drawing Sheets

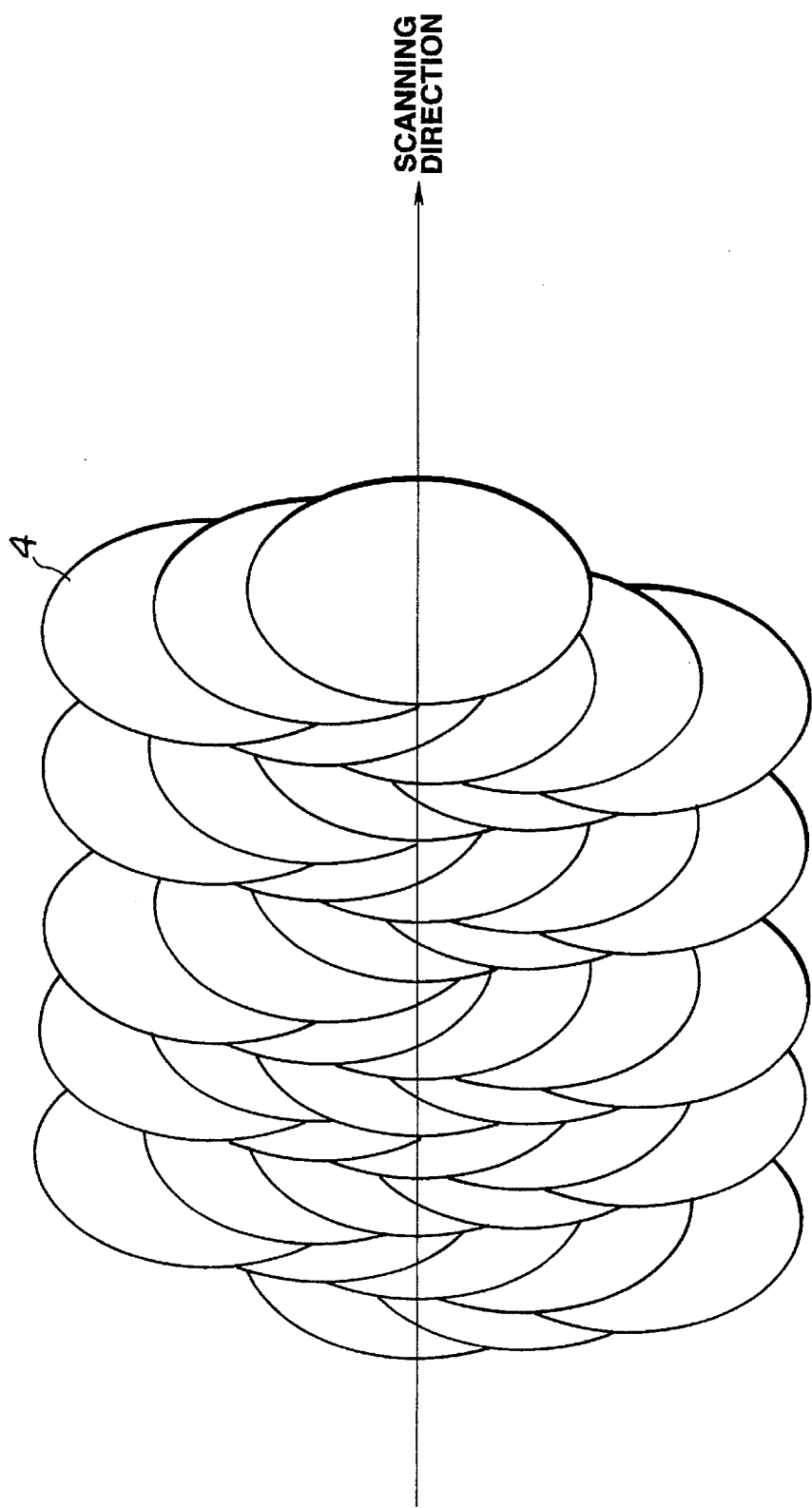

INSPECTION APPARATUS FOR DETECTING FOREIGN MATTER ON A SURFACE TO BE INSPECTED, AND AN EXPOSURE APPARATUS AND A DEVICE MANUFACTURING METHOD USING THE SAME

BACKGROUND OF THE INVENTION

1. Field of the Invention

This invention relates to an inspection apparatus for detecting foreign matter on a surface to be inspected, and a semiconductor-device manufacturing method using the apparatus. More particularly, the invention is suitable for inspecting the presence and the position of foreign matter, such as opaque dust, or the like, when the foreign matter adheres to an original, such as a reticle, a photomask, or the like, having a circuit pattern formed thereon, which is used in a semiconductor-device manufacturing apparatus, and/or a protective pellicle formed on the original.

2. Description of the Related Art

In an IC (integrated circuit) manufacturing process, IC's are, in general, manufactured by transferring a circuit pattern for exposure formed on an original, such as a reticle, a photomask, or the like, onto the surface of a wafer, on which a resist is coated, by a semiconductor printing apparatus (a stepper or a mask aligner).

At that time, if foreign matter, such as a pattern defect, dust or the like, is present on the surface of the original, the foreign matter is also transferred when the circuit pattern is transferred, thereby causing a decrease in the yield of IC manufacture.

Particularly when a circuit pattern is printed on the surface of a wafer by a step-and-repeat method using a reticle, if even a single harmful foreign matter particle is present on the surface of the reticle, the foreign matter is transferred onto the entire surface of the wafer, thereby causing a great decrease in the yield of the IC manufacturing process.

Accordingly, in the IC manufacturing process, it is indispensable to detect the presence of foreign matter on a substrate, and various kinds of inspection methods have been proposed.

In general, a method of utilizing the property of foreign matter to isotropically scatter light is mostly used.

FIG. 16 is a diagram illustrating the configuration of a principal portion of a conventional foreign matter inspection apparatus for inspecting the presence of foreign matter by detecting light scattered by the foreign matter.

In FIG. 16, a laser beam emitted from a laser light source 151 is converted into a laser beam most suitable for foreign-matter inspection by a polarizer 152, a filter 153, a collimating system 154, and the like, and is guided to a scanning optical system, comprising a scanning mirror 157, such as a polygonal mirror or the like, and an fθ lens 158, via a mirror 155. The scanning laser beam from the fθ lens 158 is condensed onto the surface of an original to be inspected 160, such as a reticle or the like, having a circuit pattern formed thereon as a scanning spot 159. By relatively moving the original 160 in a direction orthogonal to the scanning direction of the scanning spot 159 by a scanning stage system 166, the entire surface of the original 160 is scanned and inspected.

A detection system, comprising a lens system 161, an aperture 163 and a photoelectric detector 164, is disposed in a backward or lateral direction with respect to the incident direction of the laser beam. The detection system is disposed in a direction such that scattered light, generated from the circuit pattern, or the like when the laser beam is projected onto the original 160, and having particular diffraction directions, is not detected.

FIGS. 17 and 18 are diagrams schematically illustrating the positional relationship between foreign matter on the surface of the original 160, the circuit pattern and the illuminating light beam, and a signal obtained at that time, respectively. FIG. 17 shows the illuminating position on the original 160 from the illuminating side and the light-receiving side, and illustrates a state in which foreign matter 170 and a circuit pattern 171 are present on a scanning line SX of a light beam 20.

In the apparatus having the above-described configuration, when foreign matter is absent within the scanning spot 159, no scattered light is detected by the photoelectric detector 164. When foreign matter is present, scattered light is isotropically generated from the very small foreign matter, and is detected by the photoelectric detector 164. By processing a detection signal obtained at that time by a signal processing system 165, the presence of the foreign matter is inspected.

More specifically, FIG. 18 illustrates the relationship between a signal output I from the photoelectric detector 164 and the illuminating position of the light beam 20. The output I from the photoelectric detector 164 indicates a start of scanning from a starting point X0, and scattered light from the foreign matter 170 at a position X1, where the output I becomes a pulse signal exceeding a predetermined level (slice level) SL.

While the light beam 20 performs scanning from a position X2 to a position X3, the intensity of the output I does not exceed the predetermined level.

By counting pulse signals exceeding the predetermined slice level SL, the amount of foreign matter is detected. By detecting the intensity of the signal, the size of the foreign matter is determined.

In the foreign-matter inspection apparatus shown in FIG. 16, scattered light is, in some cases, generated from the circuit pattern in the direction of the detector. In the conventional method in which only information relating to the intensity of scattered light at that time is simply utilized, the intensity of scattered light from the foreign matter is assumed to be greater than that from the circuit pattern.

When the foreign matter is small, the intensity of scattered light from the circuit pattern becomes greater than that from the foreign matter. Hence, it becomes difficult to discriminate a photoelectric signal representing scattered light from the foreign matter from a photoelectric signal representing scattered light from the circuit pattern by comparing each signal with the slice level.

SUMMARY OF THE INVENTION

It is an object of the present invention to provide an inspection apparatus for detecting foreign matter on a surface to be inspected, and a semiconductor-device manufacturing method using the apparatus, in which by appropriately providing scanning conditions of a light beam on the surface to be inspected, and appropriately processing a signal representing scattered light obtained from a detection optical system for detecting scattered light from foreign matter on the surface, the presence and the position of very small foreign matter on the surface, which has previously been difficult to be detected by conventional methods, can be very precisely detected.

According to one aspect, the present invention, which achieves the above-described object, relates to an inspection apparatus comprising scanning means for scanning a surface to be inspected with a light beam in a scanning direction, the surface having a first line and a second line spaced at a predetermined interval from the first line in a direction orthogonal to the first line, detection means for detecting light generated from the surface as a result of the scanning and for producing a first signal when the light beam scans the second line, and signal processing means for processing a correlation between the first signal and the second signal obtained from the detection means and for detecting whether foreign matter exists on the surface on the basis of the correlation.

According to another aspect, the present invention relates to an inspection method comprising the steps of scanning a surface to be inspected with a light beam in a scanning direction, the surface having a first line and a second line spaced at a predetermined interval from the first line in a direction orthogonal to the first line, detecting light generated from the surface as a result of the scanning and producing a first signal when the light beam scans the first line on the surface and a second signal when the light beam scans the second line, and processing a correlation between the first signal and the second signal and detecting whether foreign matter exists on the surface on the basis of the correlation.

The foregoing and other objects, advantages and features of the present invention will become more apparent from the following description of the preferred embodiments taken in conjuction with the accompanying drawings.

BRIEF DESCRIPTION OF THE DRAWINGS

FIG. 10 is a diagram illustrating a scanning state of a light beam on an original shown in FIG. 9;

DESCRIPTION OF THE PREFERRED EMBODIMENTS

First Embodiment

Figure 1:
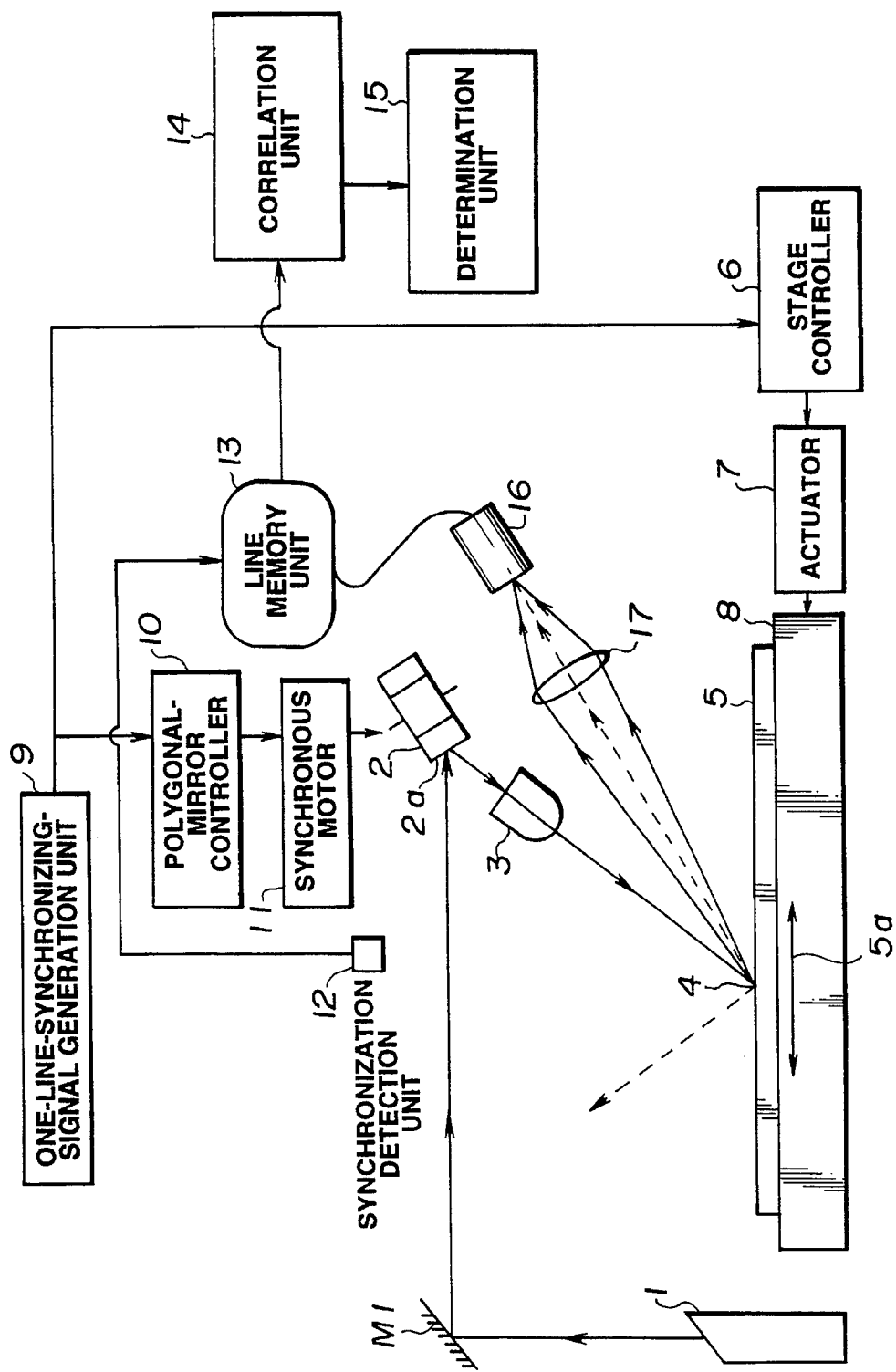
FIG. 1 is a diagram illustrating the schematic configuration of a principal portion of an inspection apparatus for detecting foreign matter on a surface to be inspected, according to a first embodiment of the present invention.

FIG. 1 is a diagram illustrating the schematic configuration of a principal portion of an inspection apparatus for detecting foreign matter on a surface to be inspected, according to a first embodiment of the present invention.

The inspection apparatus of the present embodiment inspects the state of a surface to be inspected, such as a surface of a wafer, or a surface of an original for exposure (a reticle or a photomask) used, for example, in the field of semiconductor-device manufacture. More specifically, the apparatus detects a foreign particle, such as a dust particle or the like, adhering to the surface, or a defect, such as a scratch or the like, present on the surface (these imperfections will be hereinafter generally termed "foreign matter").

The present embodiment may be applied not only to the field of semiconductor-device manufacture, but also, in general, to an apparatus for inspecting the state of a surface.

In FIG. 1, a light source 1 comprises, for example, a laser. A scanning system 2 comprises a polygonal mirror, which repeatedly reflects and deflects a light beam from the light source 1 via mirror M1.

Although in the present embodiment, the scanning system 2 comprises the polygonal mirror, it may comprise a galvano-mirror, or the like. A controller 10 controls a scanning signal relating to the scanning system 2. An actuator (a synchronous motor) 11 drives the scanning system 2. An fθ lens 3 condenses the light beam deflected by the scanning system 2 onto a surface to be inspected of an original 5 as a spot light beam 4.

In FIG. 1, the spot light beam 4 passing through the scanning system 2 and the fθ lens 3 scans the surface of the original 5 in a direction perpendicular to the plane of FIG. 1. A stage 8 mounts the original 5. An actuator (a synchronous motor) 7 drives the stage 8. A stage controller 6 controls the driving of the actuator 7.

The spot light beam 4 scans the surface of the original 5 in the above-described manner. A one-line-synchronizing-signal generation unit (circuit) 9 synchronizes the rotation of the scanning system 2 with the movement of the stage 5.

A light-receiving lens 17 condenses reflected, scattered light from the surface to be inspected of the original 5 (hereinafter simply termed, in some cases, the "orignal") as a result of the projection of the spot light beam 4, onto a photodetector 16. The photodetector 16 performs photoelectric conversion of the scattered light. The light-receiving lens 17 and the photodetector 16 constitute one element of detection means. A line memory unit 13 stores a signal representing the scattered light obtained as a result of the photoelectric conversion by the photodetector 16 for each scanning line. A synchronization detection unit 12 generates a start trigger signal for the line memory unit 13. A correlation unit 14 obtains correlation of signals from the line memory unit 13. A determination unit (circuit) 15 determines whether a substance present on the original is foreign matter or a substance other than foreign matter from the result of the correlation output from the correlation unit 14.

Next, the functions of the present embodiment will be described with reference to FIGS. 2 through 6.

Figure 2:
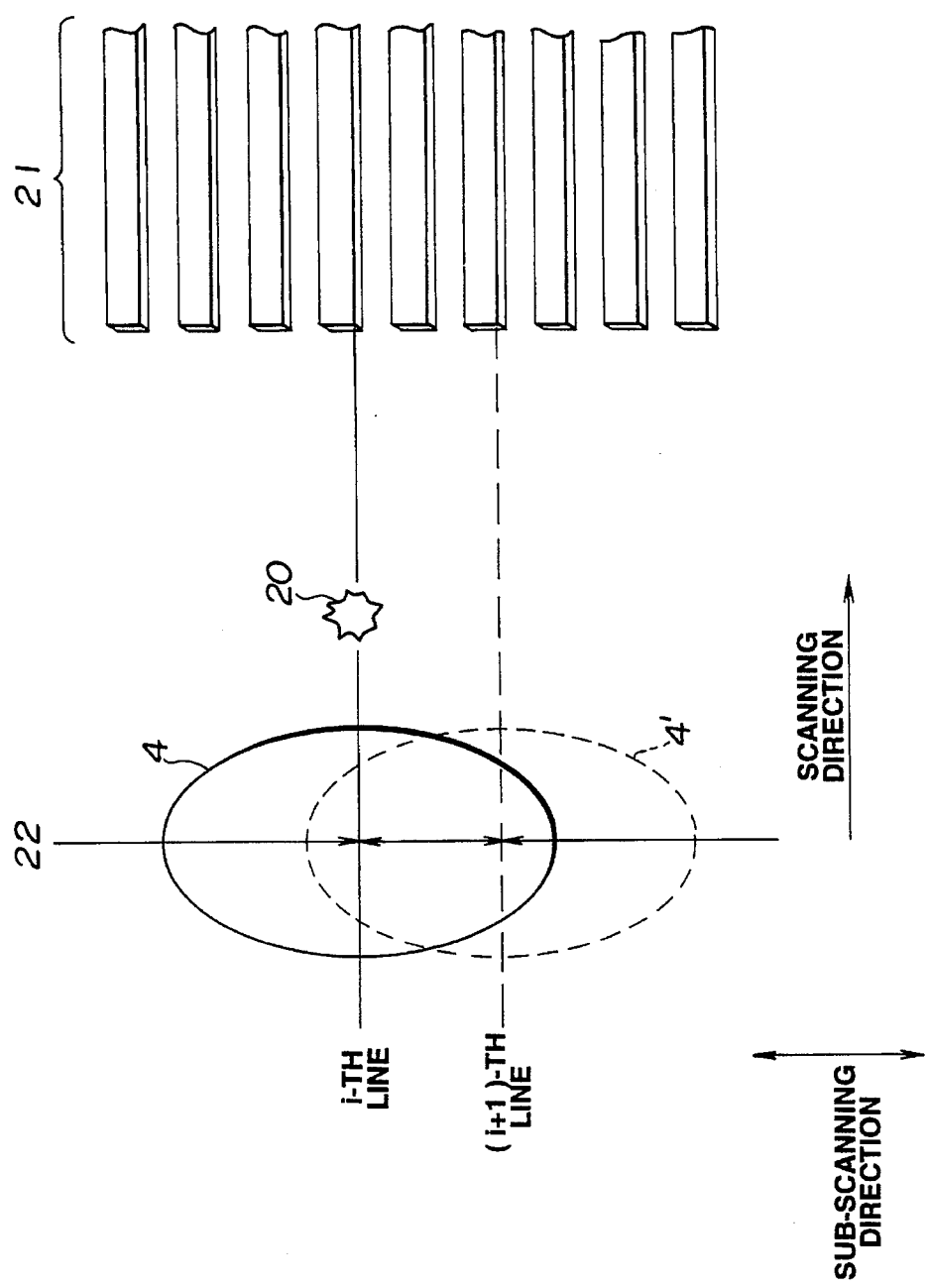
FIG. 2 is a diagram illustrating the arrangement of an illuminating spot, foreign matter and a circuit pattern on an original shown in FIG. 1.

FIG. 2 is a diagram illustrating a state in which the center of the spot light beam 4, foreign matter 20 and a circuit pattern 21 on the original 5 are present on a scanning line in the main scanning direction. There is no essential difference in the following description even if nothing is present or only one of the foreign matter 20 and the circuit pattern 21 is present on the scanning line.

FIG. 2 illustrates a case in which the size of the foreign matter 20 is smaller than the size of the circuit pattern 21.

FIG. 2 illustrates both a case in which the spot light beam 4 scans the i-th line, and a case in which the spot light beam 4' scans the (i+1)-th line.

The intensity of the cross section of the spot light beam 4 has, in general, a Gaussian distribution.

Figure 3:
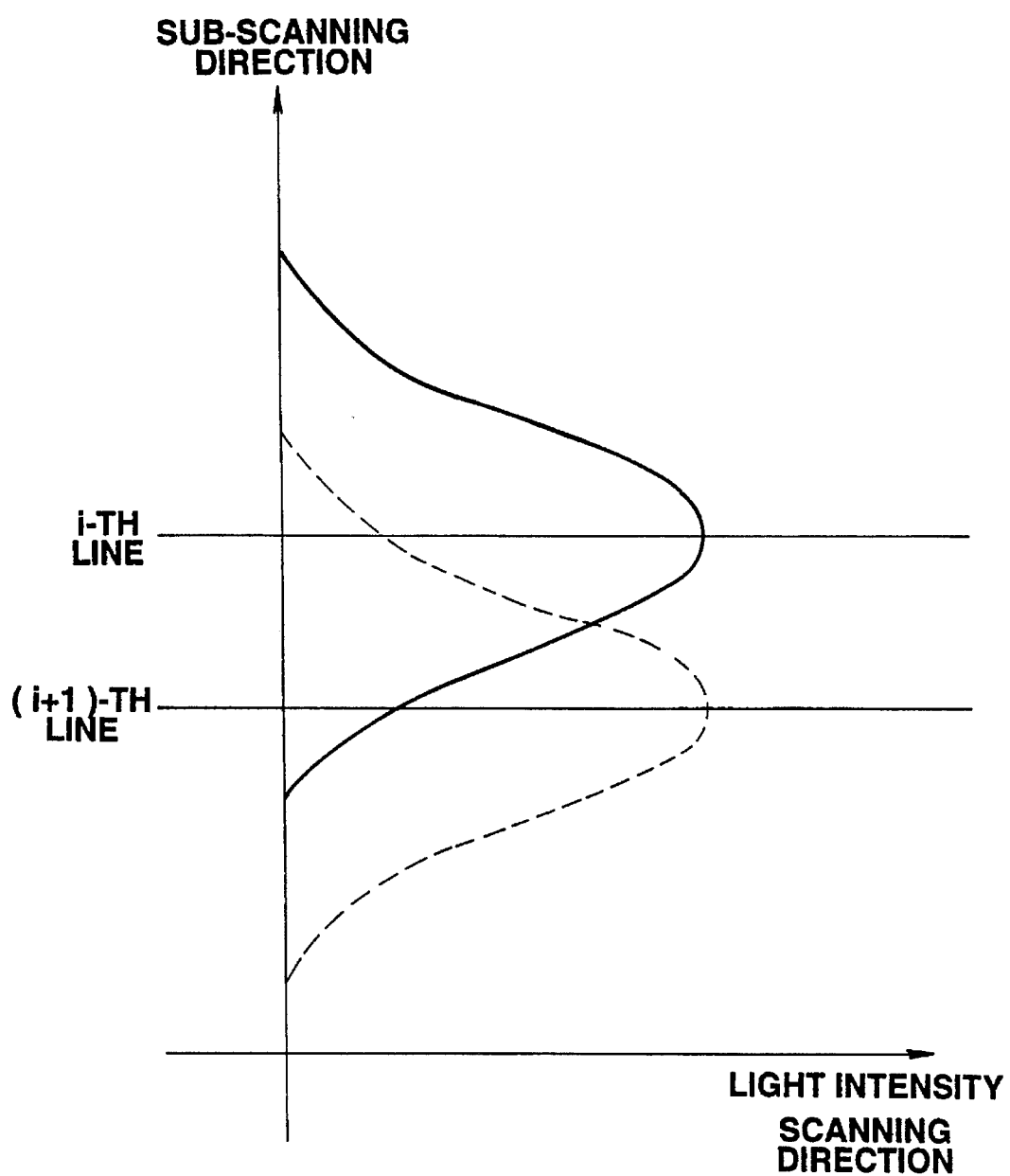
FIG. 3 is a diagram illustrating the distribution of the intensity of the illuminating spot on the original shown in FIG. 1.
Figure 4:
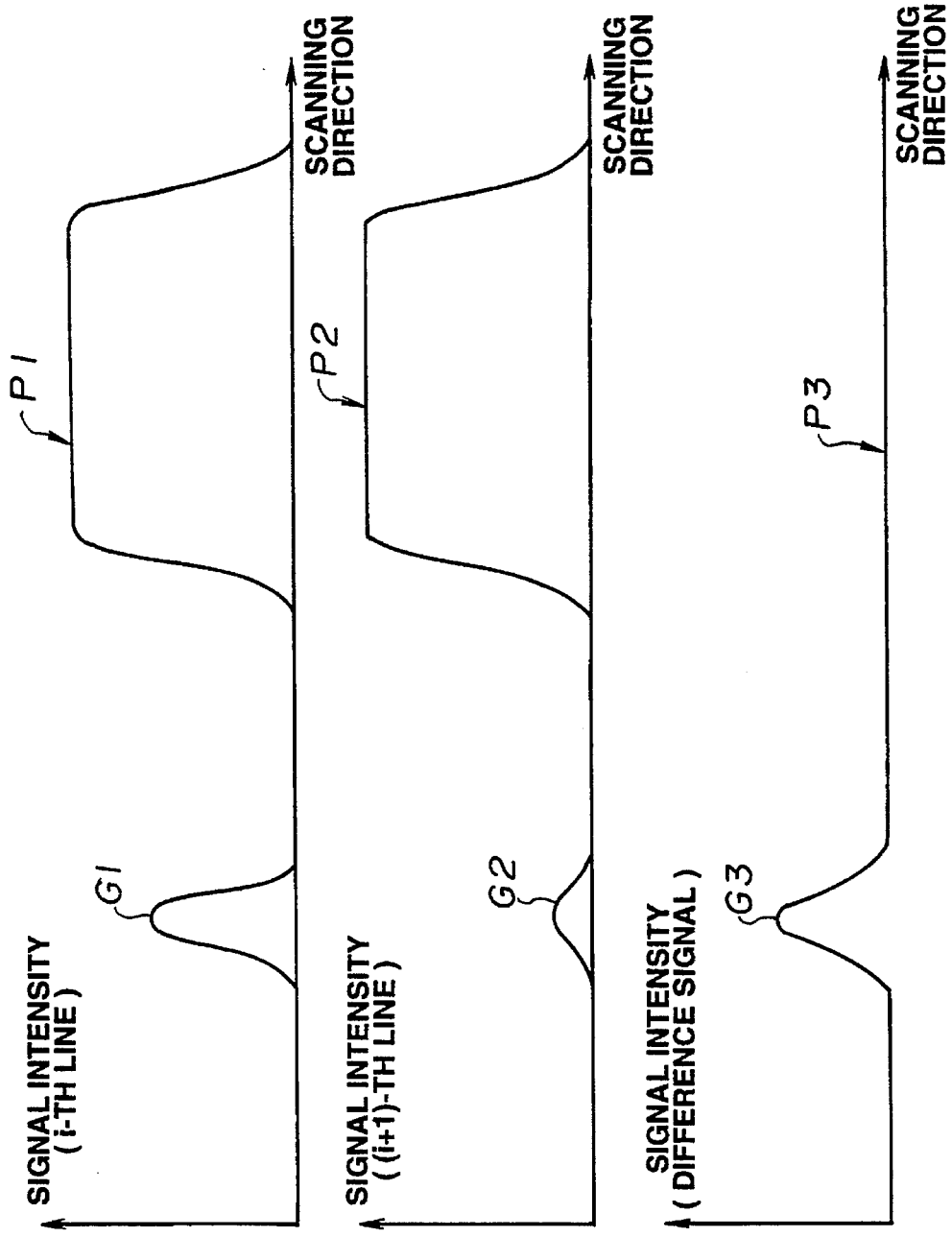
FIGS. 4(A), 4(B), 4(C), 5 and 6 are diagrams illustrating signal processing in the present embodiment.

FIG. 3 is a diagram illustrating the distribution of the intensity of the spot light beam 4 on a line 22 (in the sub-scanning direction) shown in FIG. 2. In FIG. 3, the ordinate represents the sub-scanning direction (a direction perpendicular to the main scanning direction), and the abscissa represents both the light intensity and the main scanning direction. By superposing respective trailing ends of the intensity distribution of the i-th line and the intensity distribution of the (i+1)-th line in the sub-scanning direction, the entire surface to be inspected is scanned without providing openings.

FIGS. 4(A) through 4(C) are diagrams illustrating optical signals obtained from the photodetector 16. FIGS. 4(A) and 4(B) illustrate signals obtained when first and second scattered light beams from the i-th line and the (i+1)-th line, respectively, on the original 5 scanned by the spot light beam are sensed by the photodetector 16. FIG. 4(C) illustrates the difference between the two signals obtained as a correlation between the two lines.

In FIGS. 4(A) through 4(C), symbol G represents a signal representing scattered light from the foreign matter 20, and symbol P represents a signal representing scattered light from the circuit pattern 21. FIG. 4(A) illustrates a case in which the size of the foreign matter 20 is less than a micrometer. In such a case, the peak of the signal G1 representing the first scattered light is lower than the signal P1 representing scattered light from the circuit pattern 21. Hence, the presence of the foreign matter 20 cannot be detected simply by the conventional method of using a slice level. In FIG. 4(B), the signal G2 representing the second scattered light (from the (i+1)-th line) from the foreign matter 20 differs from the signal G1 representing the first scattered light (from the i-th line) from the foreign matter 20.

On the other hand, the signal P2 representing scattered light from the circuit pattern 21 differs little from the signal P1 representing scattered light from the circuit pattern 21, because the circuit pattern 21 is much greater in size than the scanning interval in the sub-scanning direction.

Accordingly, as shown in FIG. 4(C), by obtaining the correlation (the difference in the present embodiment) between FIGS. 4(A) and 4(B), it is possible to cancel the signal relating to the circuit pattern 21, and to emphasize the signal from the foreign matter 20. By comparing the signal shown in FIG. 4(C) with a predetermined slice level, only the foreign matter 20 is selectively detected.

The correlation can be obtained not only using the difference between two signals, but also using, for example, the sum, the product and the division of two signals, so that the foreign matter can be discriminated from the circuit pattern.

Figure 5:
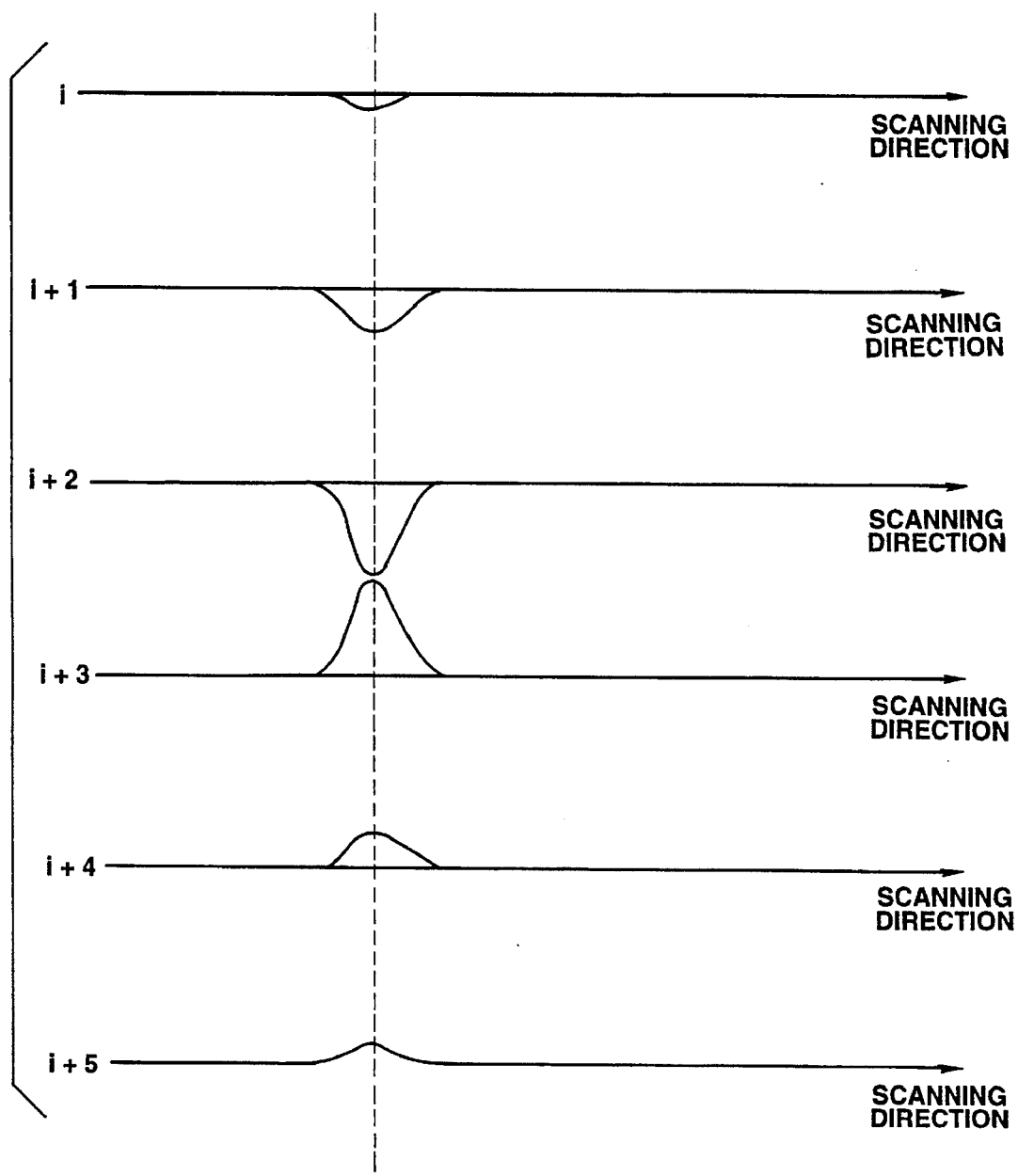

FIG. 5 illustrates signals representing scattered light from the foreign matter when the correlation (difference) between the current line and the immediately preceding line is obtained for each line from the i-th line to the (i+5)-th line. Since the size of the circuit pattern is greater than the foreign matter in the sub-scanning direction, signals representing the circuit pattern are cancelled by taking the difference between signals from two adjacent lines.

Figure 6:
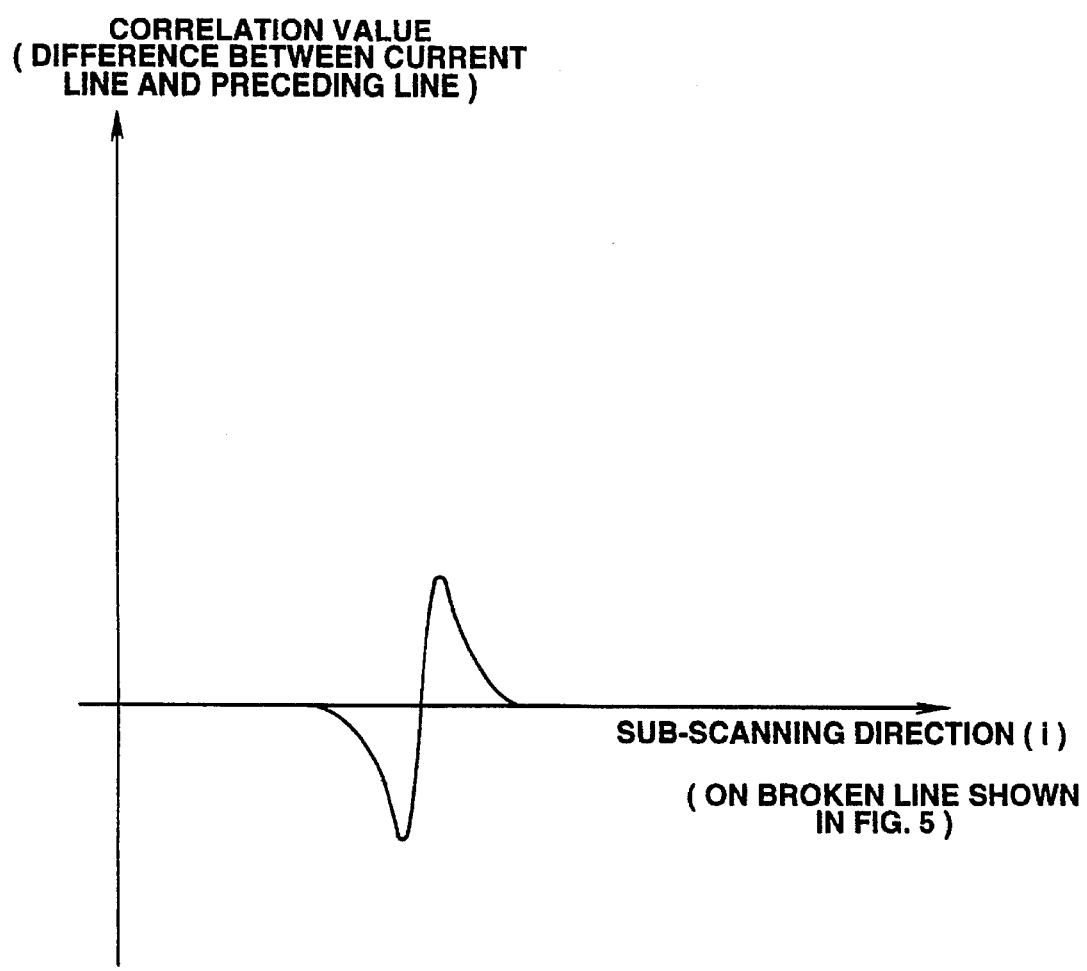

On the other hand, as described above, since the size of the foreign matter is small in the sub-scanning direction, a signal representing the foreign matter appears by taking the difference between signals from two adjacent lines, as shown in FIG. 6. In FIG. 6, the abscissa represents the sub-scanning direction (i), as indicated by broken lines shown in FIG. 5, and the ordinate represents the correlation value.

In the present embodiment, by comparing the peak value of the correlation value (difference) with a predetermined slice level, it is possible to detect small foreign matter less than a micrometer, which could not previously have been discriminated.

Next, a description will be provided of the function of each of the components shown in FIG. 1.

In FIG. 1, the light beam having the Gaussian distribution from the laser 1 is reflected by the mirror M1, and is then reflected and deflected by a reflecting surface 2a of the scanning system 2. The reflected light beam illuminates the original 5 by the function of the fθ lens 3 as the spot light beam 4. If there is no foreign matter, circuit pattern, or the like on the original 5 at the position illuminated by the light beam, the light beam is subjected to regular reflection by the original 5, and no scattered light enters the light-receiving lens 17.

On the other hand, if there is foreign matter, a circuit pattern, or the like on the original 5 at the position illuminated by the light beam, reflected, scattered light is generated from that position. A portion of the scattered light enters the light-receiving lens 17, is detected by the photodetector 16, and is subjected to photoelectric conversion.

The process of storing a photoelectric signal from the i-th line in the line memory 13 will now be described.

The polygonal-mirror controller 10 and the synchronous motor 11 are driven by a signal from the one-line-synchronizing-signal generation unit 9. When the scanning system 2 rotates, the light beam reflected by the reflecting surface 2a is deflected, so that the spot light beam 4 performs one-line illuminating scanning in a direction perpendicular to the plane of FIG. 1 while always maintaining a focused state on the surface to be inspected of the original 5 via the fθ lens 3.

During this one-line scanning, scattered light entering the photodetector 16 via the light-receiving lens 17 is continuously subjected to photoelectric conversion. At the same time, a photoelectric signal (a signal representing first scattered light) for one line from the photodetector 16 is stored in the line memory unit 13 by making a synchronizing signal from the synchronization detection unit 12 a trigger signal.

Thereafter, the stage controller 6 and the actuator 7 are driven based on a signal from the one-line-synchronizing-signal generation unit 9 to move the stage 8 in directions indicated by a two-headed arrow 5a shown in FIG. 1. In order to inspect the entire surface of the original 5, it is desirable to set the amount of the movement at that time within the range of the size of the spot light beam 4.

When scanning the (i+1)-th line, a signal representing second scattered light is stored in the line memory 13 in the same manner as in the case of the i-th line.

The correlation unit 14 reads the signal representing the first scattered light from the i-th line and the signal representing the second scattered light from the (i+1)-th line, and obtains the correlation between the two signals. By comparing the correlation value with, for example, a predetermined slice level, the determination unit 15 determines if the detected object is foreign matter.

By inspecting the entire surface of the original 5 by repeating the above-described process, foreign matter and the circuit pattern are discriminately detected. In the present embodiment, the correlation may be obtained by simply taking the difference between signals from two adjacent lines. The presence of foreign matter may be determined not only by comparing the correlation value with a slice level, but also from the waveforms of correlation values for all lines.

Next, a desciption will be provided of a method for more accurately detecting foreign matter utilizing the above-described approach.

In the present embodiment, foreign matter is discriminated from an edge of the circuit pattern parallel to the scanning direction in the following manner.

Figure 7:
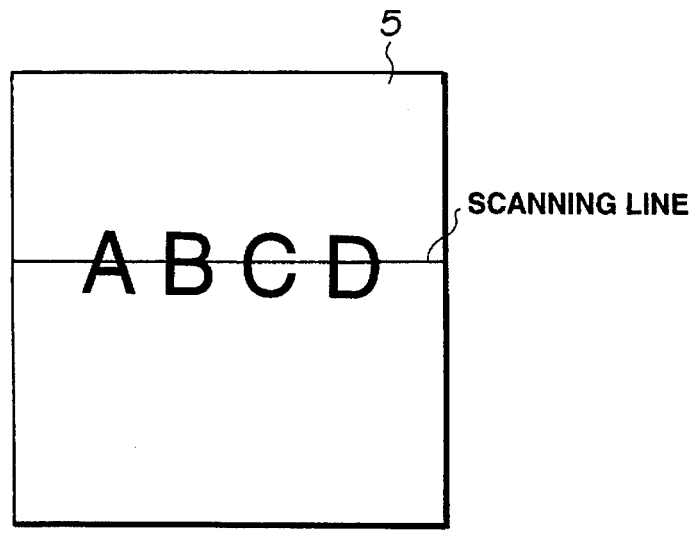
FIGS. 7(A) and 7(B) are diagrams illustrating the scanning direction of a light beam on the original in the present embodiment.
Figure 7:
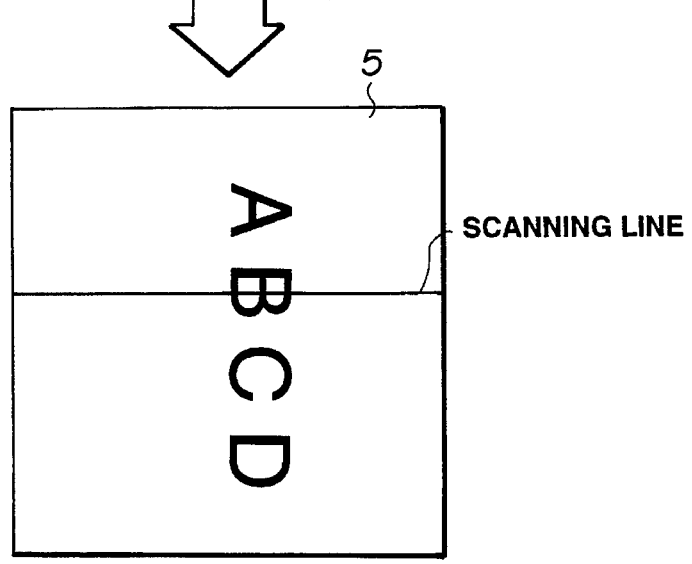

FIGS. 7(A) and 7(B) are diagrams illustrating manners of scanning the original with the spot light beam 4. As shown in FIG. 7(A), the entire surface of the original 5 is inspected, and all positions on the original 5, where it has been detetermined that foreign matter is present, are stored.

Next, as shown in FIG. 7(B), the original 5 is rotated by 90 degrees within the plane of FIG. 7(A), the entire surface of the original 5 is inspected again in the above-described manner, and all positions on the original 5, where it has been determined that foreign matter is present, are also stored. A position, where it has been determined that foreign matter is present both in the first and second inspecting operations, is determined to be a position where foreign matter is present.

In the present embodiment, foreign matter is detected utilizing the fact that the circuit pattern has a directional property and hardly has an isolated shape such as foreign matter.

As described above, in the present embodiment, erroneous detection of foreign matter is prevented by inspecting again a pattern having edges parallel to the scanning direction formed on an original after rotating the original by 90 degrees.

Although a description has been provided of a method for detecting foreign matter on an original to be inspected by discriminating the foreign matter from a circuit pattern, the inspection method of the present embodiment may also be applied to a structure in which a dust-protective layer (pellicle) is provided on an original while maintaining a space between the pellicle and the original by a supporting member.

Second Embodiment

Figure 8:
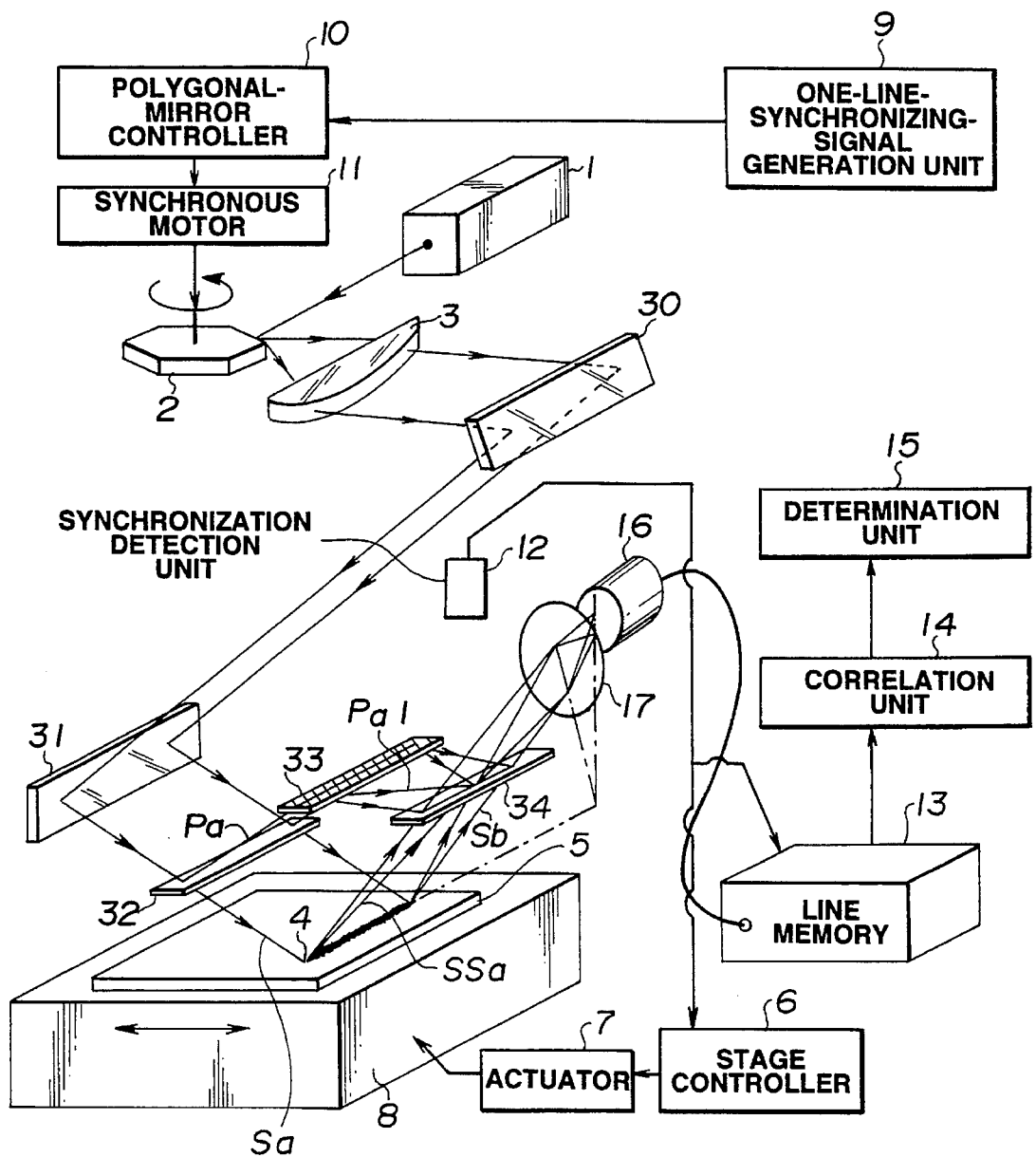
FIG. 8 is a diagram illustrating the schematic configuration of a principal portion of an inspection apparatus for detecting foreign matter on a surface to be inspected, according to a second embodiment of the present invention.

FIG. 8 is a diagram illustrating the schematic configuration of a principal portion of an inspection apparatus for detecting foreign matter on a surface to be inspected, according to a second embodiment of the present invention.

The present embodiment differs from the first embodiment in that a heterodyne interference optical system capable of detecting the presence of even smaller foreign matter is utilized. Other components are the same as those used in the first embodiment.

In FIG. 8, the same components as those shown in FIG. 1 are indicated by the same reference numerals. In FIG. 8, a light source 1 comprises a two-frequency laser. Each of mirrors 30 and 31 changes the direction of the scanning optical path. A polarizing beam splitter 32 separates the light beam from the two-frequency laser 1 at its polarizing surface to obtain reference light Pa and illuminating light Sa for an original 5. A diffraction grating 33 diffracts the reference light Pa in lateral directions. A half-mirror 34 combines the reference light Pa and scattered light Sb.

Next, a description will be provided of a method for detecting foreign matter utilizing a heterodyne method.

The laser beam from the two-frequency laser light source 1 is guided to a scanning optical system comprising a scanning mirror 2 and an fθ lens 3, and is subjected to deflecting scanning. The light beam passes through the mirrors 30 and 31, and is separated into an S-polarized laser beam (having a shift frequency $\omega$) Sa for illumination, and a P-polarized laser beam Pa (having a shift frequency $\omega+\Delta\omega$), serving as the reference light, by the beam splitter 32. The separated S-polarized laser beam Sa is focused onto the surface to be inspected of the original 5 as a spot light beam 4. Scattered light from foreign matter, a defect or a circuit pattern within the spot light beam 4 is condensed by a condensing lens 17, disposed in a lateral direction having an angle of substantially 90 degrees with respect to the incident direction of the S-polarized laser beam Sa, via a half-mirror 34 as laterally-scattered light SSa.

On the other hand, diffracted light is generated from the P-polarized laser beam Pa focused onto the diffraction grating 33. 1st-order diffracted light Pa1 from among the diffracted light is diffracted toward the half-mirror 34. The half-mirror 34 combines the 1st-order diffracted light Pa1 and the laterally-scattered light SSa. The diffraction grating 33 is designed so that the 1st-order diffracted light Pa1 is generated in a lateral direction having an angle of substantially 90 degrees with respect to the incident light beam, and so that the 1st-order diffracted light Pa1 is always combined with the laterally-scattered light SSa by the half-mirror 34 in accordance with the position of the spot light beam 4 moved by the scanning optical system.

The P-polarized component (depolarized by the foreign matter or the defect) included in the laterally-scattered light SSa combined by the half-mirror 34, and the 1st-order diffracted light Pa1 (the P-polarized component) from the diffraction grating 33 are imaged onto the sensing surface of a photodetector 16 via a condensing optical system 17 to be subjected to optical heterodyne interference. A signal based on the interference at that time is processed by a beat-signal processing system (not shown).

Although in the present embodiment, the sensing surface of the photodetector 16 is conjugate with the spot light beam 4 on the surface of the original 5, the sensing surface may be disposed at the pupillary surface of the spot light beam. Furthermore, the relationship between the P-polarized light and the S-polarized light may be inverted.

In the present embodiment, by obtaining the correlation between signals representing first and second scattered light beams from two adjacent scanning lines separated in the sub-scanning direction utilizing the heterodyne method, the presence of foreign matter is detected in the same manner as in the first embodiment.

The details of the priciple of the heterodyne method are described in U.S. patent application Ser. No. 08/076,951.

In such a method for detecting foreign matter utilizing the heterodyne method, by obtaining the correlation between signals representing scattered light beams from two adjacent lines separated in the sub-scanning direction, it is possible to obtain a high S/N ratio, and very precisely detect foreign matter. As shown in FIGS. 7(A) and 7(B), if an original to be inspected is inspected again after rotating the original by 90 degrees, it is possible to detect the presence of foreign matter while assuredly preventing erroneous detection.

Third Embodiment

Figure 9:
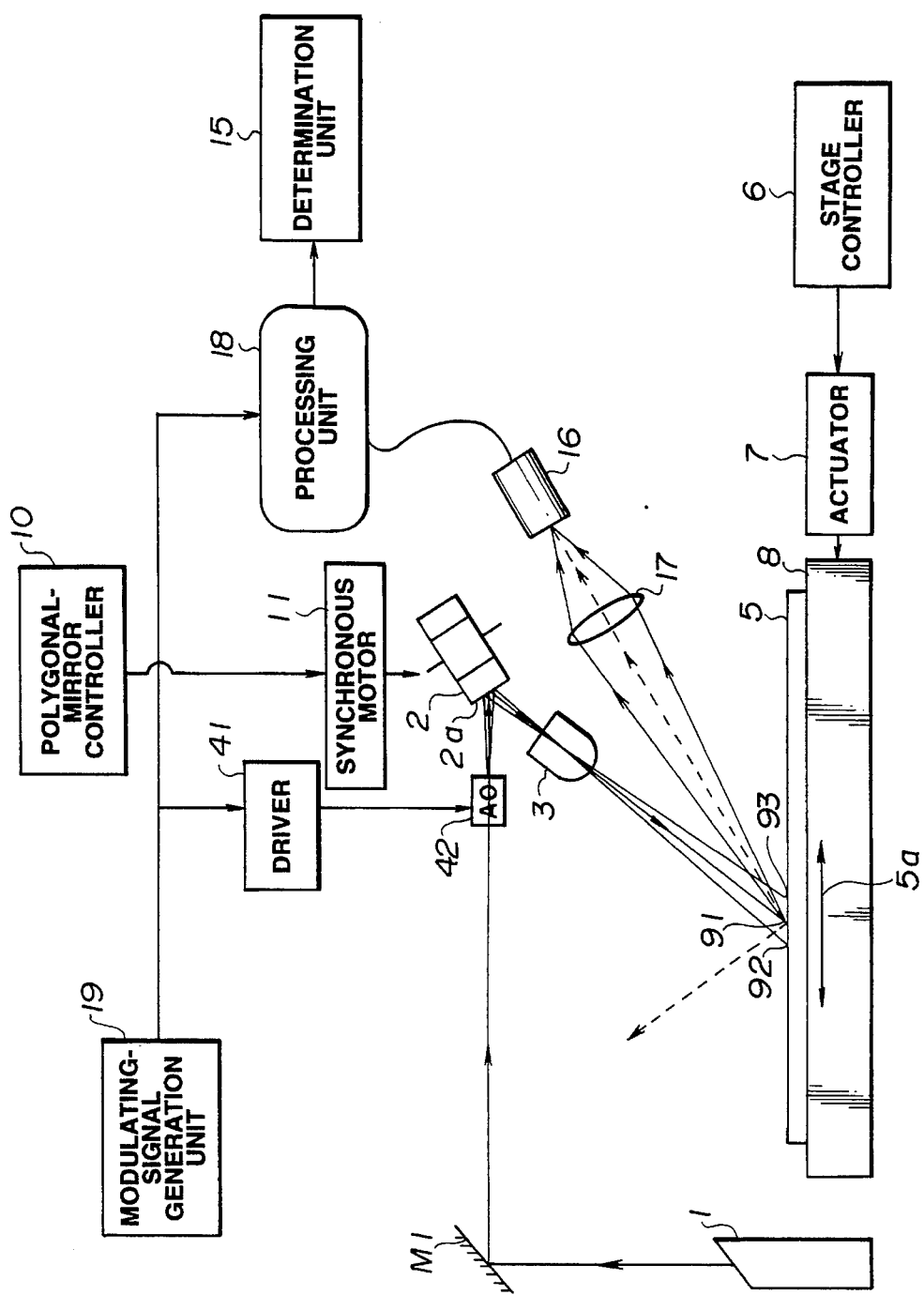
FIG. 9 is a diagram illustrating the schematic configuration of a principal portion of an inspection apparatus for detecting foreign matter on a surface to be inspected, according to a third embodiment of the present invention.

FIG. 9 is a diagram illustrating the schematic configuration of a principal portion of an inspection apparatus for detecting foreign matter on a surface to be inspected, according to a third embodiment of the present invention.

In the present embodiment, foreign matter is detected utilizing a so-called sub-scanning-direction modulation method. In the above-described first and second embodiments, the correlation between signals representing scattered light beams from two adjacent lines separated in the sub-scanning direction is obtained.

In the present embodiment, however, the same effects as in the first and second embodiments are obtained by performing very small spatial modulation in the sub-scanning direction at a high speed without obtaining the correlation between signals representing scattered light beams from two adjacent lines. In FIG. 9, the same components as those shown in FIG. 1 are indicated by the same reference numerals.

In FIG. 9, a modulating-signal generation unit 19 controls an acoustooptical element (AO) 42 and an AO driver 41, and supplies a processing unit 18 with a modulating synchronizing signal. The processing unit 18 detects a change in a signal representing scattered light subjected to photoelectric conversion by the photodetector 16 in the sub-scanning direction while being supplied a trigger signal from the modulating-signal generation unit 19. A determination unit 15 determines whether the detected object is foreign matter or an object other than foreign matter based on a result of processing supplied from the processing unit 18.

Next, a description will be provided of the functions of the present embodiment. In FIG. 9, the light beam having the Gaussian distribution from the laser 1 is reflected by the mirror M1, and is then reflected and deflected by the reflecting surface 2a of the scanning system 2. The reflected light beam illuminates the original 5 by the function of the fθ lens 3 as the spot light beam 4. If there is no foreign matter, circuit pattern, or the like on the original 5 at the position illuminated by the light beam, the light beam is subjected to regular reflection by the original 5, and no scattered light enters the light-receiving lens 17.

On the other hand, if there is foreign matter, a circuit pattern, or the like on the original 5 at the position illuminated by the light beam, reflected scattered light is generated from that position. A part of the scattered light enters the light-receiving lens 17, is detected by the photodetector 16, and is subjected to photoelectric conversion.

Next, a description will be provided of the operation of one scanning line. When the modulating-signal generation unit 19 drives the AO 42 via the AO driver 41, the light beam is diffracted by the AO 42, and is thereby periodically polarized within the plane of FIG. 9, whereby the illuminating position on the original 5 oscillates between a position 92 and a position 93 back and forth from a position 91.

On the other hand, when the scanning system 2 is rotated by the polygonal-mirror controller 10 and the synchronous motor 11, the light beam reflected by the reflecting surface 2a is deflected, so that the spot light beam 4 performs one-line illuminating scanning in a direction perpendicular to the plane of FIG. 9 while always maintaining a focused state on the surface of the original 5 via the fθ lens 3.

FIG. 10 is a diagram illustrating the loci of the illuminating light beam 4 on a part of a scanning line on the surface of the original 5. The spot light beam 4 oscillates with an amplitude less than the size of the spot light beam 4 in the sub-scanning direction while performing scanning in the (main) scanning direction. The frequency of the oscillation is such that the spot light beam 4 performs at least one reciprocating motion while it moves by one spot size in the scanning direction. During this one-line scanning, scattered light entering the photodetector 16 via the light-receiving lens 17 is continuously subjected to photoelectric conversion.

At the same time, a photoelectric signal from the photodetector 16 is processed by the processing unit 18 by making a synchronizing signal from the modulating-signal generation unit 19 a trigger signal. FIGS. 11(A) through 11(D) are diagrams illustrating an output signal from the photodetector 16 and processed signals in this embodiment.

Figures 11A, 11B, 11C, 11D:
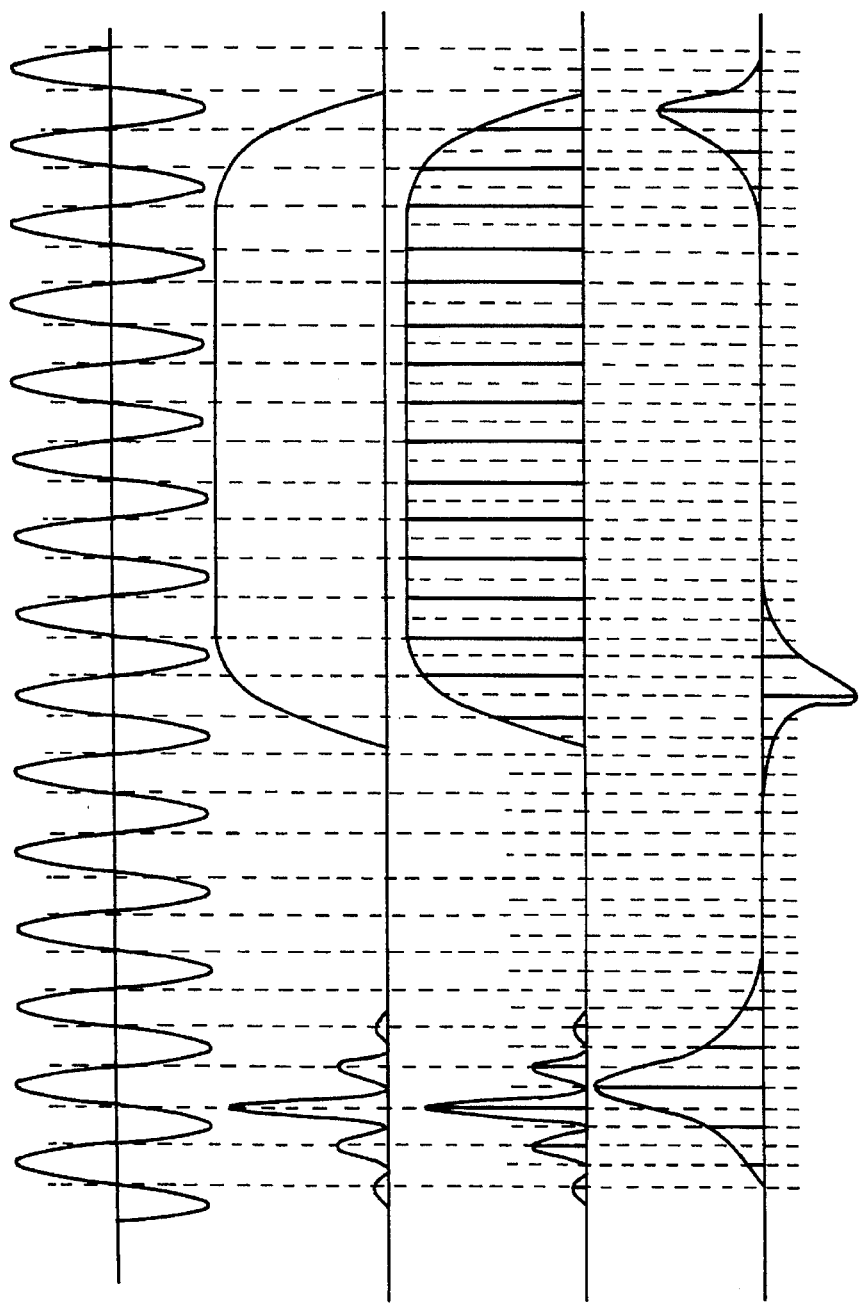
FIGS. 11(A), 11(B), 11(C) and 11(D) are diagrams illustrating signal processing in the third embodiment.

FIG. 11(A) illustrates a modulating signal from the modulating-signal generation unit 19, and FIG. 11(B) illustrates an output from the photodetector 16. As in the case of FIG. 2, it is assumed that foreign matter is present at a preceding position on one scanning line, and a circuit pattern is present after the foreign matter. Scattered light from the foreign matter is modulated with a period twice the period of the modulating frequency. On the other hand, scattered light from the circuit pattern is not modulated, and keeps the original waveform.

FIGS. 11(C) and 11(D) illustrate processing for discriminating the foreign matter from the circuit pattern utilizing the above-described fact. FIG. 11(C) illustrates a result of sampling the signal with a period four times the period of the signal from the modulating-signal generation unit 19. FIG. 11(D) illustrates a result of obtaining the difference between signal values while skipping every other value of the signal sampled in the above-described manner. The determination unit 15 discriminates a signal from the foreign matter from a signal from an object other than the foreign matter based on this result, for example, by comparing each signal with a slice level. In the present embodiment, the foreign matter can also be discriminated from an object other than the foreign matter by another method (for example, waveform discrimination).

Thereafter, the stage 8 is moved in the directions of two-headed arrow 5a by driving the stage controller 8 and the actuator 7. It is desirable to set the amount of the movement within the size of the spot light beam 4 in order to inspect the entire surface of the original 5.

By inspecting the entire surface of the original 5 by repeating the above-described processing, the foreign matter and the circuit pattern are discriminately detected.

Fourth Embodiment

Figure 12:
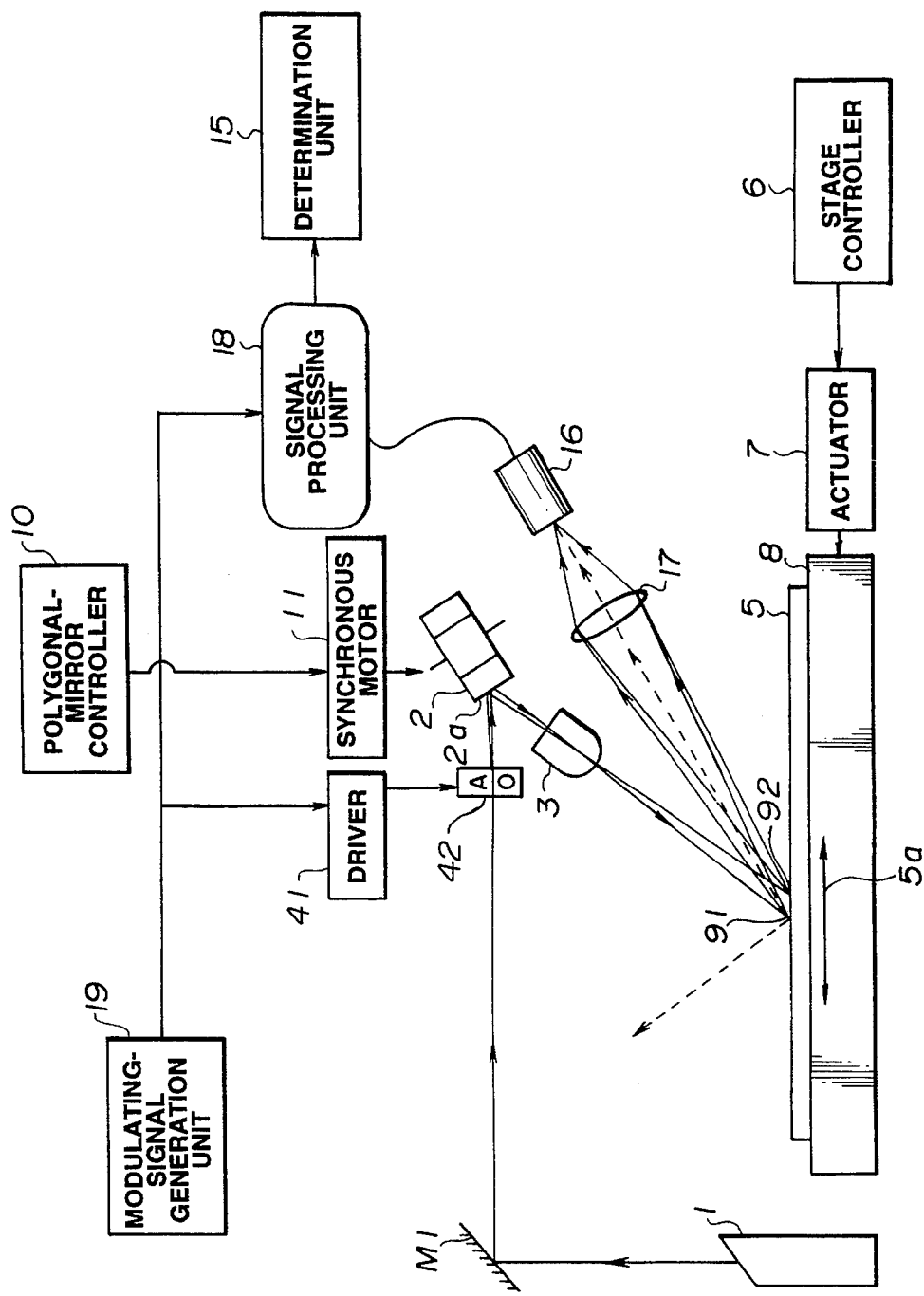
FIG. 12 is a diagram illustrating the schematic configuration of a principal portion of an inspection apparatus for detecting foreign matter on a surface to be inspected, according to a fourth embodiment of the present invention.

FIG. 12 is a diagram illustrating the schematic configuration of a principal portion of an inspection apparatus for detecting foreign matter on a surface to be inspected, according to a fourth embodiment of the present invention.

In the present embodiment, foreign matter is detected utilizing a so-called sub-scanning-direction two-beam modulation method.

In the third embodiment, the same effects as in the first and second embodiments are obtained by performing very small spatial modulation in the sub-scanning direction at a high speed. In the present embodiment, the same effects as in the first through third embodiments are obtained by alternately projecting two beams, separated from each other by a predetermined distance in the sub-scanning direction, onto the surface of the original 5.

The configuration of the apparatus of the present embodiment is substantially the same as that of the third embodiment shown in FIG. 9. Hence, a description of respective components will be omitted.

The function of the present embodiment is the same as that of the third embodiment in that the light beam having the Gaussian distribution from the laser 1 illuminates and scans the original 5.

Next, a description will be provided of the operation of one scanning line. When the modulating-signal generation unit 19 drives the AO 42 via the AO driver 41, the light beam is diffracted by the AO 42, and is thereby polarized within the plane of FIG. 12, whereby the illuminating position on the original S is alternately switched between a position 91 and a position 92.

On the other hand, when the scanning system 2 is rotated by the polygonal-mirror controller 10 and the synchronous motor 11, the light beam reflected by the reflecting surface 2a is deflected, so that the spot light beam 4 performs one-line illuminating scanning in a direction perpendicular to the plane of FIG. 12 while always maintaining a focused state on the surface of the original 5 via the fθ lens 3.

Figure 13:
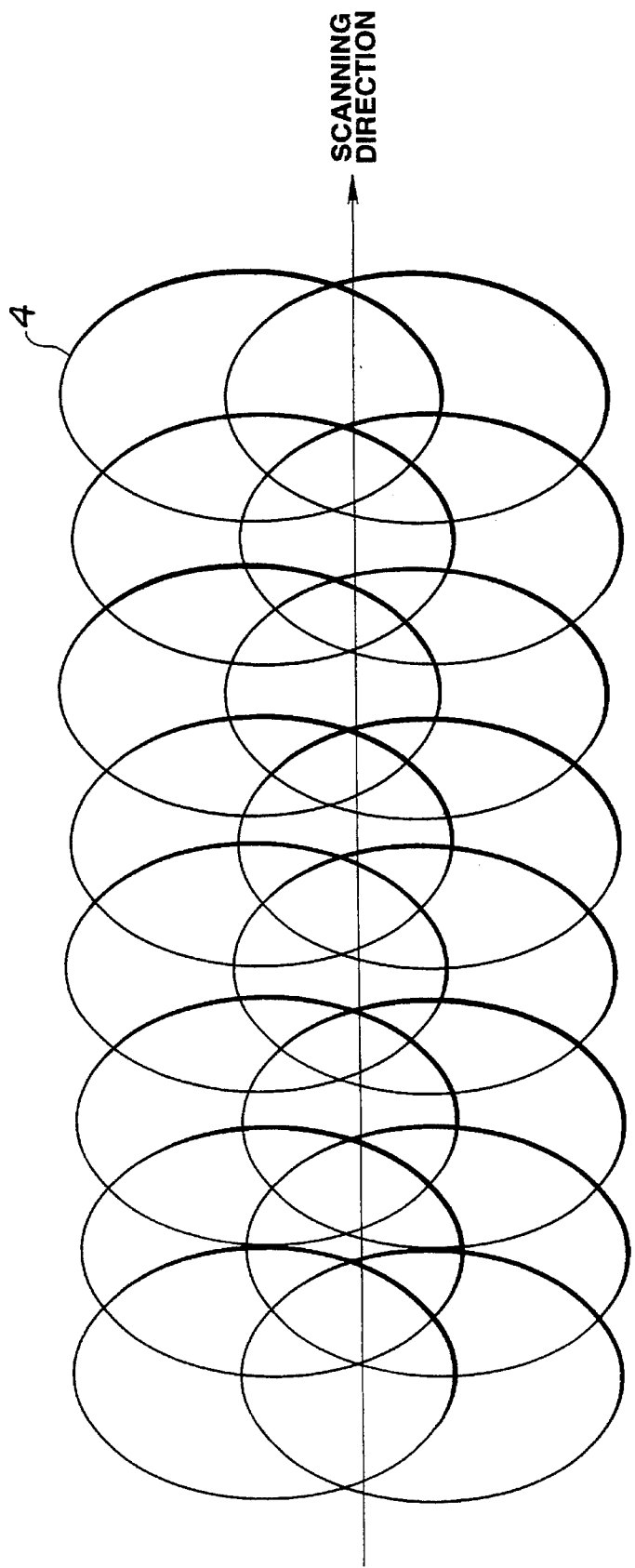
FIG. 13 is a diagram illustrating a scanning state of a light beam on an original shown in FIG. 12.

FIG. 13 is a diagram illustrating the loci of the illuminating light beam 4 on a portion of a scanning line on the surface of the original 5. The spot light beam 4 is alternately switched with an amplitude less than the size of the spot light beam 4 in the sub-scanning direction while performing scanning in the (main) scanning direction. The frequency of the oscillation is such that the spot light beam 4 performs at least one reciprocating motion while it moves by one spot size in the scanning direction. A signal representing scattered light obtained from the photodetector 16 is processed in the same manner as in the third embodiment.

Hereafter, the stage 8 is moved in the directions of two-headed arrow 5a by driving the stage controller 6 and the actuator 7. It is desirable to set the amount of the movement within the size of the spot light beam 4 in order to inspect the entire surface of the original 5.

By inspecting the entire surface of the original 5 by repeating the above-described processing, the foreign matter and the circuit pattern are discriminately detected.

According to the above-described embodiments, the following effects can be obtained.

(i) Foreign matter having a size smaller than about 0.3 μm on a reticle, which has previously been difficult to be detected, can be detected with excellent sensitivity while being discrimated from a circuit pattern.

(ii) Scattered light generated in a lateral direction with respect to illuminating light is condensed and detected with high sensitivity while omitting light diffracted by a circuit pattern. Hence, foreign matter, a defect, or the like can be inspected with a high S/N ratio and high sensitivity.

Fifth Embodiment

Figure 14:
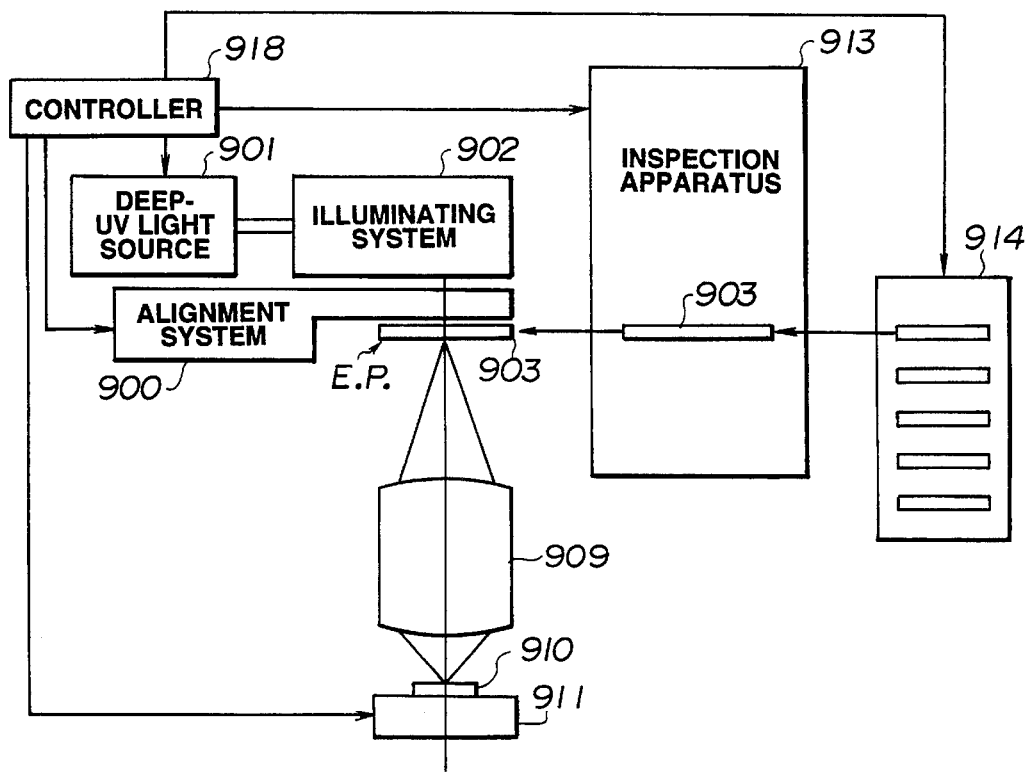
FIG. 14 is a diagram illustrating the schematic configuration of a pricipal portion of a semiconductor-device manufacturing system according to a fifth embodiment of the present invention.

FIG. 14 is a diagram illustrating the schematic configuration of a principal portion of a semiconductor-device manufacturing system according to a fifth embodiment of the present invention.

The present embodiment relates to a system for manufacturing semiconductor devices by printing a circuit pattern formed on an original, such as a reticle, a photomask, or the like, onto a wafer. The system roughly includes an exposure apparatus, an apparatus for accommodating originals, an apparatus for inspecting originals, and a controller. These apparatuses are installed in a clean room.

In FIG. 14, a deep-UV light source 901 comprises, for example, an excimer laser. A unified illumination system 902 illuminates an original 903 set at an exposure position E.P. from above with a predetermined NA (numerical aperture). A projection lens 909 projects and prints a circuit pattern formed on the original 903 onto a wafer 910, such as a silicon substrate, or the like. In the projection/printing operation, exposure is repeated while moving the wafer 910 at every shot in accordance with a stepwise movement of a moving stage 911. An alignment system 900 aligns the wafer 910 with the original 903 before the exposure operation. The alignment system 900 includes at least one microscope system for observing originals.

The above-described units constitute the exposure apparatus.

An original-accommodating apparatus 914 accommodates a plurality of originals. An inspection apparatus (a foreign-matter inspection apparatus) 913 detects the presence of foreign matter on an original, and includes the configuration described in the foregoing embodiments. The inspection apparatus 913 detects foreign matter on an original before the original is taken out of the accommodating apparatus 914 and is set at the exposure position E.P.

The principle and the operation of the foreign-matter inspection at that time is the same as those described in the foregoing embodiments. A controller 918 controls the sequences of the entire system, such as operation instructions for the accommodating apparatus 914 and the inspection apparatus 913, alignment, exposure and stepwise movement of a wafer, which are basic operations of the exposure apparatus, and the like.

A description will now be provided of the process for manufacturing semiconductor devices using the system of the present embodiment.

First, an original 903 to be used is taken out of the accommodating apparatus 914, and is set in the inspection apparatus 913.

Then, the inspection apparatus 913 inspects the original 903 for foreign matter. When it has been confirmed that no foreign matter is present, the original 903 is set at the exposure position E.P. of the exposure apparatus.

Then, the semiconductor wafer 910, serving as an object to be exposed, is set on the moving stage 911. By a step-and-repeat method, the pattern on the original 903 is subjected to reduced projection and is exposed on each region of the semiconductor wafer 910 while moving the wafer 910 at each shot in accordance with the stepwise movement of the moving stage 911. This operation is repeated.

When the entire surface of the semiconductor wafer 910 has been exposed, this wafer is accommodated, and a new wafer is supplied. By the step-and-repeat method, the pattern on the orginal 903 is also exposed onto this wafer.

The exposed wafer is subjected to known processing, such as development, etching, and the like, by an apparatus separate from the present system. Thereafter, semiconductor devices are manufactured passing through assembling processing, such as dicing, wire bonding, packaging, and the like.

According to the present embodiment, it is possible to manufacture highly-integrated semiconductor devices having very fine circuit patterns which have previously been difficult to manufacture.

Sixth Embodiment

Figure 15:
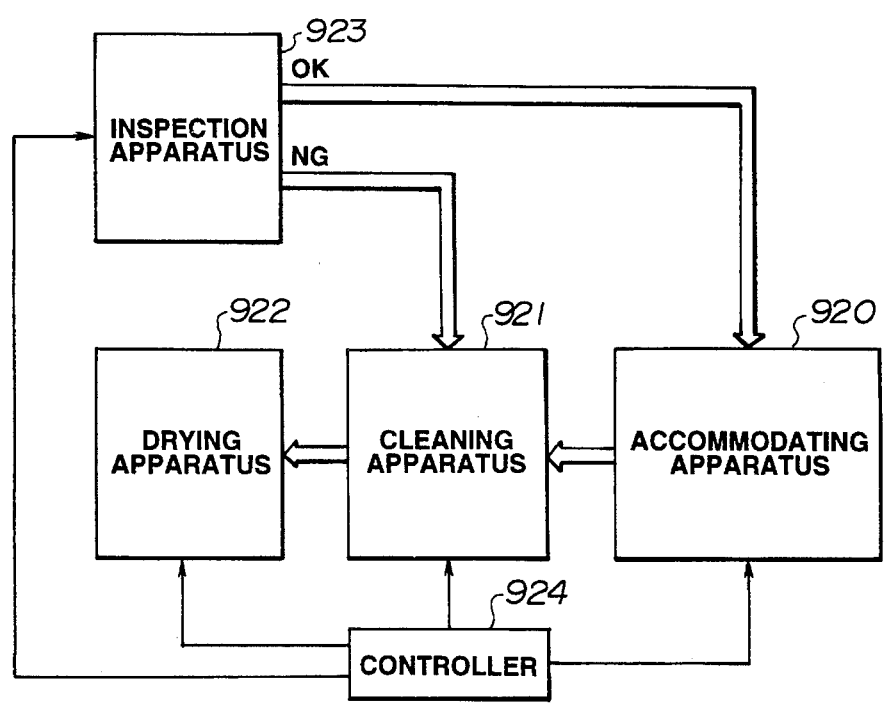
FIG. 15 is a block diagram of a system for cleaning and inspecting an original.
Figure 16:
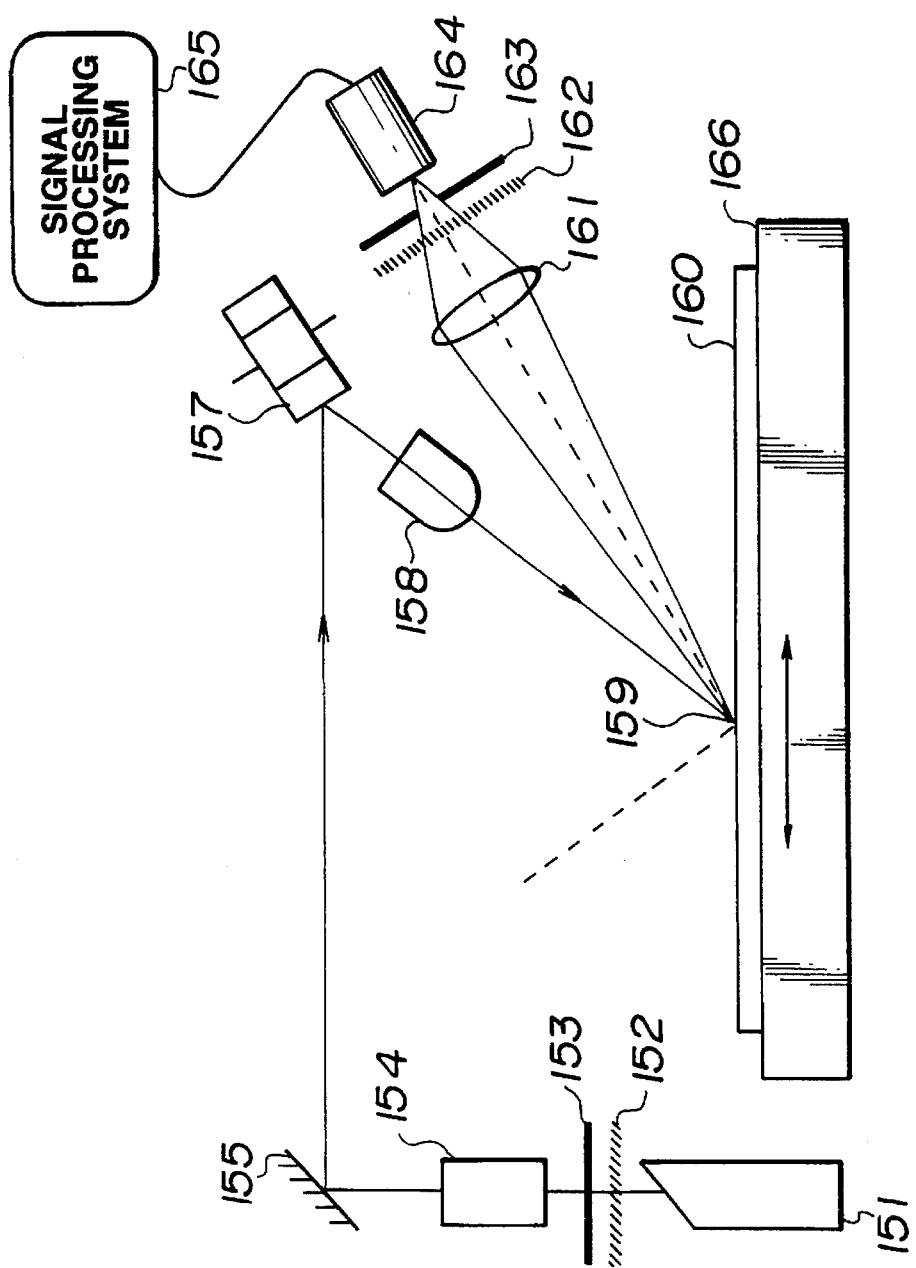
FIG. 16 is a diagram illustrating the schematic configuration of a principal portion of a conventional foreign-matter inspection apparatus.
Figure 17:
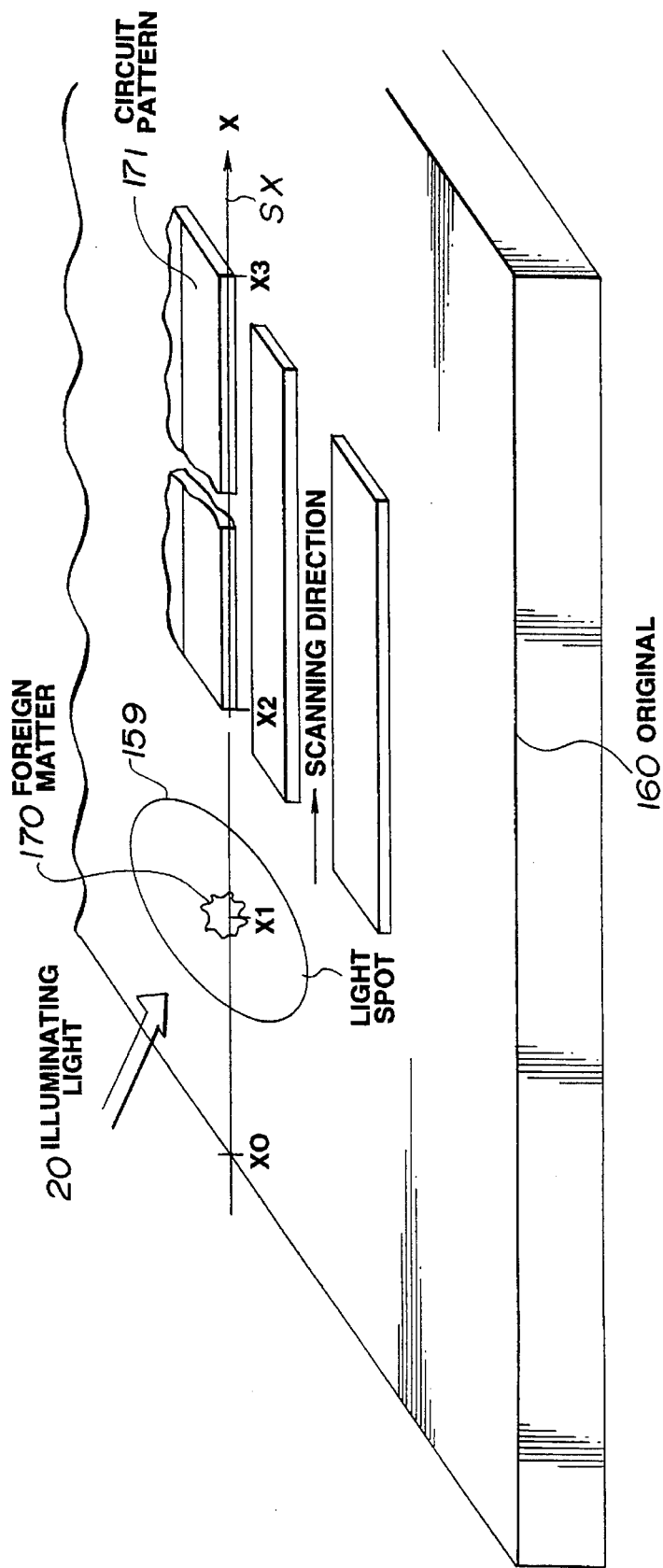
FIG. 17 is an enlarged perspective view of a part of FIG. 16.
Figure 18:
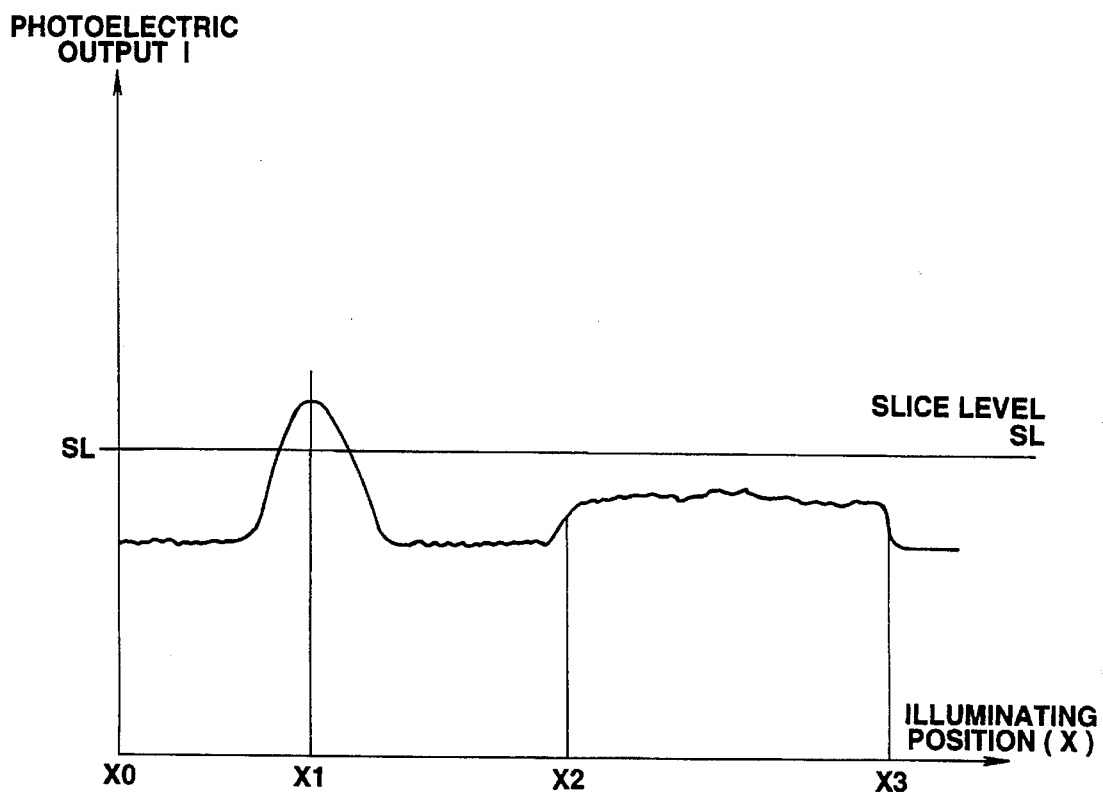
FIG. 18 is a diagram illustrating signal processing performed by the conventional apparatus shown in FIG. 16.

FIG. 15 is a block diagram illustrating a system for cleaning and inspecting originals in order to manufacture semiconductor devices. The system roughly includes an accommodating apparatus for originals, a cleaning apparatus, a drying apparatus, an inspection apparatus and a controller. These apparatuses are installed in a clean chamber.

In FIG. 15, an original-accommodating apparatus 920 accommodates a plurality of originals, and supplies an original to be cleaned. A cleaning apparatus 921 cleans the supplied original with pure water. A drying apparatus 922 dries the cleaned original. An inspection apparatus 923 for originals includes the configuration of any of the above-described embodiments, and inspects the cleaned original for foreign matter. A controller 924 performs the sequence control of the entire system.

The operation of the system will now be described. First, an original to be cleaned is taken out of the original-accommodating apparatus 920, and is supplied to the cleaning apparatus 921. The original cleaned in the cleaning apparatus 921 is sent to the drying apparatus 922, where the original is dried. After being dried, the original is sent to the inspection apparatus 923, where the original is inspected for foreign matter using the method of any of the above-described embodiments.

When it has been confirmed that foreign matter is absent as a result of the inspection, the original is returned to the accommodating apparatus 920. When it has been confirmed that foreign matter is present, the original is returned to and cleaned in the cleaning apparatus 921. After being dried in the drying apparatus 922, the original is inspected again by the inspection apparatus 923. This processing is repeated until foreign matter is completely removed. The completely cleaned original is returned to the accommodating apparatus 920.

Thereafter, the cleaned original is set in an exposure apparatus, and a circuit pattern formed on an original is printed onto a semiconductor wafer, whereby semiconductor devices are manufactured. It is thereby possible to manufacture highly integrated semiconductor devices having very fine circuit patterns, which have previously been difficult manufacture.

The individual components shown in outline or designated by blocks in the drawings are all well known in the foreign-matter inspection apparatus arts and their specific construction and operation are not critical to the operation or best mode for carrying out the invention.

While the present invention has been described with respect to what is presently considered to be the preferred embodiments, it is to be understood that the invention is not limited to the disclosed embodiments. To the contrary, the present invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. An inspection apparatus, comprising:

scanning means for scanning a surface to be inspected with a light beam in a scanning direction, the surface having a first line and a second line spaced at a predetermined interval from the first line in a direction orthogonal to the first line, wherein the predetermined interval between the first line and the second line is less than the size of a light beam spot projected onto the surface by said scanning means;

detection means for detecting light generated from the surface as a result of the scanning and for producing a first signal when the light beam scans the first line on the surface and a second signal when the light beam scans the second line; and signal processing means for processing a correlation between the first signal and the second signal obtained from said detection means and for detecting whether foreign matter exists on the surface.

2. An apparatus according to claim 1, wherein said detection means detects scattered light generated from the surface.

3. An apparatus according to claim 1, wherein said scanning means comprises a laser light source for generating the light beam and a scanning optical system for scanning the surface with the light beam.

4. An apparatus according to claim 1, wherein said signal processing means comprises means for calculating the difference between the first signal and the second signal.

5. An apparatus according to claim 1, wherein said signal processing means comprises a first memory and a second memory for storing the first signal and the second signal, respectively.

6. An apparatus according to claim 1, wherein said scanning means projects a light beam including two frequency components having different directions of polarization, and said detection means performs heterodyne detection on the basis of the frequency components and directions of polarization of the light beam.

7. An apparatus according to claim 1, wherein the surface to be inspected comprises a reticle surface on which a transfer pattern is formed.

8. An apparatus according to claim 7, wherein the predetermined interval between the first line and the second line is less than the width of the transfer pattern formed on the reticle surface, and is less than the size of a light beam spot projected onto the reticle surface by said scanning means.

9. An apparatus according to claim 1, wherein the surface to be inspected comprises a pellicle surface.

10. An apparatus according to claim 1, further comprising means for cleaning the surface when foreign matter has been detected.

11. An apparatus according to claim 1, further comprising exposing means for exposing the surface when foreign matter has not been detected.

12. An inspection method, comprising the steps of:

scanning a surface to be inspected with a light beam in a scanning direction, the surface having a first line and a second line spaced at a predetermined interval from the first line in a direction orthogonal to the first line, wherein the predetermined interval between the first line and the second line is less than the size of a light beam spot projected onto the surface in said scanning step;

detecting light generated from the surface as a result of the scanning and producing a first signal when the light beam scans the first line on the surface and a second signal when the light beam scans the second line; and processing a correlation between the first signal and the second signal and detecting whether foreign matter exists on the surface on the basis of the correlation.

13. A method according to claim 12, further comprising a step of cleaning the surface when foreign matter has been detected.

14. A method according to claim 12, further comprising a step of exposing the surface when foreign matter has not been detected.

15. A method according to claim 12, wherein said detecting step detects scattered light generated from the surface.

16. A method according to claim 12, further comprising using a laser light source for generating the light beam and a scanning optical system for scanning the surface with the light beam.

17. A method according to claim 12, further comprising calculating the difference between the first signal and the second signal to detect whether foreign matter exists on the surface.

18. A method according to claim 12, further comprising using a first memory and a second memory for storing the first signal and the second signal, respectively.

19. A method according to claim 12, wherein said scanning step comprises projecting a light beam including two frequency components having different directions of polarization, and further comprising performing heterodyne detection on the basis of the frequency components and directions of polarization of the light beam.

20. A method according to claim 12, wherein the surface to be inspected comprises a reticle surface on which a transfer pattern is formed.

21. A method according to claim 20, wherein the predetermined interval between the first line and the second line is less than the width of the transfer pattern formed on the reticle surface, and is less than the size of a light beam spot projected onto the reticle surface in said scanning step.

22. A method according to claim 12, wherein the surface to be inspected comprises a pellicle surface.

23. An inspection apparatus, comprising:

scanning means for scanning a surface to be inspected with a light beam in a scanning direction, the surface having a first line and a second line spaced at a predetermined interval from the first line in a direction orthogonal to the first line, wherein said scanning means comprises means for spatially modulating the light beam in a direction crossing the scanning direction;

detection means for detecting light generated from the surface as a result of the scanning and for producing a first signal when the light beam scans the first line on the surface and a second signal when the light beam scans the second line; and signal processing means for processing a correlation between the first signal and the second signal obtained from said detection means and for detecting whether foreign matter exists on the surface, wherein said signal processing means calculates a substantial correlation between the first signal relative to the first line and the second signal relative to the second line, in synchronization with the modulation of the light beam.

24. An inspection apparatus, comprising:

scanning means for scanning a surface to be inspected with a light beam in a scanning direction, the surface having a first line and a second line spaced at a predetermined interval from the first line in a direction orthogonal to the first line, wherein said scanning means scans the surface in a first direction to inspect a portion of the surface, and scans the surface in a second direction, different from the first direction, to inspect the same portion of the surface;

detection means for detecting light generated from the surface as a result of the scanning and for producing a first signal when the light beam scans the first line on the surface and a second signal when the light beam scans the second line; and signal processing means for processing a correlation between the first signal and the second signal obtained from said detection means and for detecting whether foreign matter exists on the surface.

25. An inspection method, comprising the steps of:

scanning a surface to be inspected with a light beam in a scanning direction, the surface having a first line and a second line spaced at a predetermined interval from the first line in a direction orthogonal to the first line, wherein said scanning step comprises spatially modulating the light beam in a direction crossing the scanning direction, and calculating a substantial correlation between the first signal relative to the first line and the second signal relative to the second line, in synchronization with the modulation of the light beam;

detecting light generated from the surface as a result of the scanning and producing a first signal when the light beam scans the first line on the surface and a second signal when the light beam scans the second line; and processing a correlation between the first signal and the second signal and detecting whether foreign matter exists on the surface on the basis of the correlation.

26. An inspection method, comprising the steps of:

scanning a surface to be inspected with a light beam in a scanning direction, the surface having a first line and a second line spaced at a predetermined interval from the first line in a direction orthogonal to the first line, wherein said scanning step comprises scanning the surface in a first direction to inspect a portion of the surface, and scanning the surface in a second direction, different from the first direction, to inspect the same portion of the surface;

detecting light generated from the surface as a result of the scanning and producing a first signal when the light beam scans the first line on the surface and a second signal when the light beam scans the second line; and processing a correlation between the first signal and the second signal and detecting whether foreign matter exists on the surface on the basis of the correlation.

* * * * *